United States Patent [19]

Greaves et al.

[11] Patent Number: 5,245,010
[45] Date of Patent: Sep. 14, 1993

[54] POLYPEPTIDE OF HERPES SIMPLEX VIRUS VMW 65 PROTEIN

[75] Inventors: Richard F. Greaves, London; Peter F. J. O'Hare, Surrey, both of England

[73] Assignee: National Research Development Corporation, London, England

[21] Appl. No.: 820,658

[22] PCT Filed: Jul. 25, 1990

[86] PCT No.: PCT/GB90/01143
§ 371 Date: Jan. 17, 1992
§ 102(e) Date: Jan. 17, 1992

[87] PCT Pub. No.: WO91/01329
PCT Pub. Date: Feb. 7, 1991

[30] Foreign Application Priority Data

Jul. 25, 1989 [GB] United Kingdom ............... 8917029

[51] Int. Cl.$^5$ ............................................. C07K 7/00
[52] U.S. Cl. ................... 530/327; 435/69.1; 530/826; 530/389.4; 930/224
[58] Field of Search .............. 530/326, 327, 389.4, 530/826; 514/13, 14; 435/69.1; 930/224

[56] References Cited

PUBLICATIONS

G. Werstuck & J. P. Capone "Mutational Analysis of Herpes Simplex Virus ... Vms 65" Gene 75:213-224, 1989.
S. Triezenberg et al. "Functional Dissection of VP16 ..." Genes & Development 2:718-729 1988.
R. Greaves et al., J. Virology 63(4) 1641-1650 Apr. 1989.
B. M. Datia et al. Nature 321:439-441 May 22, 1986.
Pellett et al., "Nucleotide sequence and predicted ..." Proc. Natl. Acad. Sci. USA, vol. 82, 1985, pp. 5870-5874.

*Primary Examiner*—Robert J. Hill, Jr.
*Assistant Examiner*—L. Spector
*Attorney, Agent, or Firm*—Nixon & Vanderhye

[57] ABSTRACT

A polypeptide which inhibits the replication of Herpes Simplex Virus and like viruses, which has the amino acid sequence of consecutive amino acids of HSV protein Vmw 65 and comprises the sequence 367 to 373:

Ala Arg Thr Lys Asn Asn Tyr (identified as SEQ ID NO: 1) or a conservatively modified variant thereof, its therapeutic use and antibodies thereto.

2 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 30 amino acids
( B ) TYPE: amino acid
( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
( A ) ORGANISM: Herpes simplex virus
( B ) STRAIN: hsv-1

( i x ) FEATURE:
( A ) NAME/KEY: Peptide
( B ) LOCATION: 8..13
( D ) OTHER INFORMATION: /label=region1
/ note="homologous region"

( x i ) SEQUENCE DESCRIPTION: SEQ ID NO:1:

| Arg | Glu | His | Ala | Tyr | Ser | Arg | Ala | Arg | Thr | Lys | Asn | Asn | Tyr | Gly | Ser |
|---|---|---|---|---|---|---|---|---|---|---|---|---|---|---|---|
| 1 | | | | 5 | | | | | 10 | | | | | 15 | |
| Thr | Ile | Glu | Gly | Leu | Leu | Asp | Leu | Pro | Asp | Asp | Asp | Ala | Pro | | |
| | | | 20 | | | | | 25 | | | | | 30 | | |

POLYPEPTIDE OF HERPES SIMPLEX VIRUS VMW 65 PROTEIN

BACKGROUND OF THE INVENTION

1. Field of the Invention

This invention relates to a polypeptide which inhibits the replication of Herpes Simplex Virus (HSV) and like viruses and its therapeutic use against infections of such viruses.

2. Description of the Prior Art

HSV exists as several serotypes of which HSV-1 is one which is clinically significant in relation to cold sores. HSV-1 is a DNA virus which is transcribed and replicated within the cell nucleus. As with many other viruses, the genes are transcribed into mRNA at different times. Certain important genes which are the first to be transcribed are denoted immediate-early (IE) or "α". Their transcription is enabled by promoter sequences which lies to the 5' end or upstream of the ATG start codon of the gene. Further upstream from the promoter the IE genes have a distinctive nucleotide sequence which is a consensus (common) sequence TAATGARAT (where R=purine, i.e. can be G or A).

The IE genes of HSV are induced by a component of the virion, first identified by M. E. M. Campbell, J. W. Palfreyman and C. M. Preston, Journal of Molecular Biology 180, 1–19 (1984), as "Vmw 65". Vmw 65, which has also been referred to as VP16, is a tegument protein which lies between the viral membrane and the capsid. Vmw 65 is said to be "trans-acting" or "transactivating". This language indicates merely that it is some soluble factor which acts on the viral DNA to regulate it. Yet another name for Vmw 65 is the α-Trans Inducing Factor or α-TIF, meaning that it acts on the viral DNA to induce transcription of the IE (α) genes.

M. E. M. Campbell et al., loc. cit. speculated that Vmw 65 might bind to the DNA in the TAATGARAT region, either directly or indirectly by modifying a host cell polypeptide. Later work, beginning with that of T. M. Kristie and B. Roizman, Proc. Natl. Acad. Sci. USA, 84, 71–75 (1987), has shown that the TAATGARAT region, which is termed a "cis-acting site" or the α-Trans Induction Cis-acting (α-TIC) site, does not bind directly to Vmw 65, but does bind to one or more host cell proteins. Various groups of workers have identified host cell proteins which bind both to the TAATGARAT region and to Vmw 65. They have been variously designated as "α-H1", "HC3", "octamer-binding protein", "OTF-1" and "TAATGARAT Recognition Factor" (TRF), all of which are probably identical. The TRF nomenclature is used in this specification.

Current knowledge is summarised by C. I. Ace et al., J. Virology 63, 2260–2269 (May 1989). Vmw 65 indicates the induction of IE genes by associating with cellular proteins, to form a complex known as IEC or TRF.C, which is able to bind specifically to DNA sequences which include TAATGARAT. In other words, IE gene induction involves a complex which is at least ternary between, at least, Vmw 65, TRF and a TAATGARAT region sequence.

It would be desirable to block the formation of this complex and thereby block induction of IE gene transcription of HSV. C. I. Ace et al., supra, have demonstrated that a virus mutant which lacks the ability to form such a complex with Vmw 65 and TRF replicates very poorly at low multiplicity of infection (MOI). Low MOI would be encountered clinically. Attempts have therefore been made to identify regions of Vmw 65 responsible for complex formation. It might then be possible to synthesise a short polypeptide which would compete with Vmw 65 in the formation of the complex.

S. J. Triezenberg, R. C. Kingsbury and S. L. McKnight, Genes & Development 2, 718–729 (1988) explored Vmw 65 structure/function with an assay for IE gene transcriptional induction and for the ability of Vmw 65 deletion mutants to inhibit IE transcriptional induction by normal Vmw 65. They showed that if the carboxy terminus of Vmw 65 was deleted, the protein would no longer induce IE transcription, but reported that this deleted protein could prevent IE induction by normal Vmw 65. Using various deleted forms of Vmw 65 they showed that the boundaries for this inhibitory activity (i.e. inhibition of normal Vmw 65 when the two are together) mapped at the N-terminus somewhere between amino acids 56 and 74 and at the C-terminus somewhere between 380 and 393. Since their proposition is that the competitive inhibitory activity is due to an interaction with a cellular intermediate, they claim that these boundaries may be the boundaries for interaction with this cellular intermediate. Note that the assay was for gene transcription, i.e. essentially for an "end product". Therefore, the inhibitory activity could actually take place at any of a wide range of steps, e.g. by saturating sites for transport of the virus into the nucleus of the cell.

G. Werstuck and J. P. Capone, Gene 75, 213–224 (1989), have also explored Vmw 65 structure and function using measurements of the expression of a cat gene linked to an IE promoter region as an assay for the transcriptional induction function of Vmw 65. They found a total loss of IE induction activity when 4 or 5 amino acids were inserted into the Vmw 65 coding sequence at amino acids 178, 215, 335, 369 or 471 or when Vmw 65 was deleted in any of the following regions: amino acids 26–140, 26–177, 26–240, 142–177, 174–240, 179–412, 242–412, 331–412 and 331–470. In addition, in a similar assay to that used by Triezenberg et al, they examined the ability of the deleted mutants of Vmw 65 to competitively inhibit the IE induction function of normal Vmw 65. Competitive inhibition was obtained with mutants deleted from 331–470, 331–412, 242–412 or 186–490, indicating that the boundary of this competitive inhibiting activity mapped at an amino acid lower than 186. It is noteworthy and illustrative of the complications resulting from using this sort of assay to attempt to relate structure of Vmw 65 to function, that the boundary mapped for competitive inhibitory activity by Werstuck and Capone differs substantially from that mapped by Triezenberg et al., supra.

R. Greaves and P. O'Hare, Journal of Virology 63, 1641–1650 (April 1989), directly demonstrated that the acidic C-terminal domain of Vmw 65 (from amino acids 403 to the C-terminus) is not required for complex formation but that within the sequence of amino acids 317–403 there is a region which is required for complex formation.

C. I. Ace et al., J. Gen. Virology 69, 2595–2605 (1988) and Journal of Virology 63, 2260–2269 (May 1989) have performed biochemical studies of DNA-protein complex formation. This group has shown that insertion of a linker encoding a small number of amino acids (usually 4), at any of several of positions in the Vmw 65 sequence, directly prevents the ability of these altered proteins to form a complex with TRF. Amongst these, an insertion at amino acid 379 prevented the ability to form complex. In parallel, they confirmed that those mutants unable to form complex with TRF were unable to induce IE expression.

SUMMARY OF THE INVENTION

It has now been found that TRF.C (complex) formation is inhibited by a polypeptide which consists of or includes the region of about amino acids 366 or 367 to 373 of Vmw 65. The boundaries of the critical region have not yet been defined with absolute precision and it cannot be ruled out that one might be able to dispense with one or two amino acids at either end of this chain. More probably, however, the polypeptide would have to be made longer to achieve the best inhibition, particularly at the C-terminal (373) end. Particularly preferred is a polypeptide which consists of or includes the amino acids 360 to 390, especially 366 or 367 to 388, 389 or 390.

Relevant amino acid sequence is as follows (identified as SEQ ID NO: 1):

| Arg 360 | Glu | His | Ala | Tyr | Ser | Arg | Ala | Arg | Thr |
|---|---|---|---|---|---|---|---|---|---|
| Lys 370 | Asn | Asn | Tyr | Gly | Ser | Thr | Ile | Glu | Gly |
| Leu 380 | Leu | Asp | Leu | Pro | Asp | Asp | Asp | Ala | Pro |

For additional sequence, see S. J. Triezenberg et al., Genes & Development 2, 718-719 (1988) at page 719.

In order to put some positive limits on the invention, to distinguish readily between the short-chain polypeptides contemplated herein and the longer sequences which are the subject of experimentation in the prior art referred to above, it is intended that the polypeptides of the invention should not be longer than 40 amino acids, most preferably not longer than 30. These are purely arbitrary numbers.

The invention includes the polypeptide per se, together with conservatively modified variants thereon, and its use as an inhibitor of any virus which depends for its action on a Vmw 65-like protein, but, of course, particularly for Herpes Simplex Viruses and especially HSV type 1.

The invention further includes antibodies to the polypeptides of the invention and their use as inhibitors of viral replication and for other purposes.

DESCRIPTION OF THE PREFERRED EMBODIMENTS

The inventive concept has at its heart an experimental showing that the polypeptide consisting of amino acids 360-373 is an inhibitor of IE gene induction in HSV. The notion that this sequence could be cut back at its N-terminal end and/or extended at its C-terminal end derives from other evidence. In brief, experiments have been carried out with deletion mutants of Vmw 65 made by deletions which start at the C-terminus and extend progressively towards the N-terminus. These mutants were made in the Vmw 65 gene by progressively chewing back the gene from its 3'-end with Bal31, inserting a stop codon in all three reading frames, expressing the gene and testing the expression products by Western blotting with an antibody to an N-terminal epitope of Vmw 65 in order to detect the Vmw 65 mutants. The mutants were then tested for their ability to form the TRF.C, by a DNA binding assay as described by R. Greaves and P. O'Hare, supra, with the following results:

| Portion deleted | Forms complex (TRF.C) |
|---|---|
| 389 - C terminus | Yes |
| 385 - C terminus | Only very weakly |
| 381 - C terminus | No |

Moreover, it has been found that the 21 amino acid sequence from about 367 to 387 shows significant homology (about 50%) with the terminal protein of the *B. subtilis* bacteriophage φ29. This protein is involved in the formation of an initiation complex for initiation of φ29 DNA replication in vivo via protein-protein and protein-DNA interactions. For a recent summary of work on this phage and for references, see A. Zaballos et al., Gene 63 113-121 (1988).

Polypeptides of the invention can be prepared by routine methods of synthesis, well known to those in the peptide field. For use as inhibitors of HSV replication in humans the polypeptides can be administered parenterally in a suitable inert diluent at a dose typically within the range 0.1 to 15 mg. per day. Topical administration, as an ointment or cream is also contemplated.

The invention also includes antibodies to the polypeptides of the invention, whether polyclonal, monoclonal or made by antibody engineering. Such antibodies are potentially of therapeutic value to block the Vmw 65 directly and also useful in the diagnosis of herpes virus infections. For example, they could be used to capture the Vmw 65 for a two site or sandwich assay, a labelled antibody directed to another epitope of Vmw 65 being used for detection of the captured Vmw 65. In order to produce the antibodies of the invention it is convenient to attach to the N-terminal end a cysteine residue, thereby providing an -SH termination. This enables the polypeptide to be coupled to (say) bovine serum albumin for the raising of antibodies, which can be immobilised in a conventional manner.

The invention is particularly applicable to the human Herpes Simplex Viruses Type 1 and 2 and to other herpes viruses which depend on Vmw 65 or a protein which is closely homologous in the relevant amino acid region for binding to a cellular factor to form a complex which induces IE gene expression.

The following Example illustrates the invention.

EXAMPLE

The experiment for demonstration of peptide inhibition of TRF-Vmw 65 complex assembly was as follows.

A nuclear extract of HeLa cells was prepared exactly as described by Dignam et al., Nucl. Acids. Res. 11 1475-1489, (1983) (This is a standard protocol for the preparation of extracts containing cellular DNA binding proteins). Polypeptides from Vmw 65 amino acids were synthesised by Cambridge Research Biochemicals Ltd., Cambridge, UK, under contract, in accordance with the sequence set forth above. 1 µl volumes of phosphate buffered saline containing increasing amounts (100 ng, 500 ng, 1 µg, 2.5 µg, 5 µg) of three different polypeptides (amino acids 119-134; 160-176; 360-373) were added to a standard amount of HeLa cell nuclear extract (1 µl extract per 2 µg polypeptide). After incubation at 20° C. for 30 minutes a 1 µl sample of Vmw 65 protein, purified as described by P. O'Hare et al., EMBO J. 7:4231-4238 (1988) was added to the extract polypeptide mixtures and incubation continued for a further 5 minutes in a buffer containing 25 mM HEPES pH 7.9, 1 mM EDTA, 5 mM DTT, 100 mM KCl, 0.05% NP40 10% glycerol, and 2 μg of salmon sperm DNA. A $^{32}$P radioactively labelled probe present in excess and encompassing nucleotides −171 to −149 (numbered starting upstream of the site of mRNA transcription: the TAATGARAT sequence is at −162 to −154) of the immediate-early IE110K gene of HSV-1 was then added and incubation continued for a further 25 minutes. The products were then separated on 4% non-denaturing polyacrylamide gels at 200 volts for 2 hours. These procedures are essentially as described in O'Hare and Goding, Cell 52: 435-445 (1988). On autoradiography, the gels showed high molecular weight bands due to the radiolabelled TRF and TRF/Vmw 65 complexes when there was zero concentration of any polypeptide. The addition of the 119-134 and 160-176 polypeptides had no effect on the appearance of either of these bands. In the presence of the 360-373 polypeptide, the radiolabelled TRF/Vmw 65 band became fainter with increasing concentration, becoming undetectable at concentrations between 500 ng and 1 μg. The radiolabelled band representing the TRF alone did not alter in intensity.

---

---

We claim:

1. An isolated polypeptide of up to 30 consecutive amino acids of the Herpes Simplex virus protein Vmw65, consisting of or including the sequence (N-terminal to C-terminal) Arg Glu His Ala Tyr Ser Arg Ala Arg Thr Lys Asn Asn Tyr.

2. A polypeptide according to claim 1 which further consists of or includes flanking amino acids within the 360 to 390 sequence:

| Arg 360 | Glu | His | Ala | Tyr | Ser | Arg | Ala | Arg | Thr |
|---|---|---|---|---|---|---|---|---|---|
| Lys 370 | Asn | Asn | Tyr | Gly | Ser | Thr | Ile | Glu | Gly |
| Leu 380 | Leu | Asp | Leu | Pro | Asp | Asp | Asp | Ala | Pro |

(identified as SEQ ID NO: 1).

* * * * *